(12) United States Patent
Lee et al.

(10) Patent No.: US 11,048,255 B2
(45) Date of Patent: Jun. 29, 2021

(54) GOLF CART SYSTEM CAPABLE OF CHANGING TRAVELING MODE ACCORDING TO WHETHER ENTERING GOLF COURSE IS POSSIBLE AND GOLF CART CONTROL METHOD USING THE SAME

(71) Applicant: TT&G Co., Ltd., Daegu (KR)

(72) Inventors: Bae Hee Lee, Daegu (KR); Jong Soo Park, Daegu (KR); Chi Hun Yu, Daegu (KR)

(73) Assignee: TT&G CO., LTD., Daegu (KR)

( * ) Notice: Subject to any disclaimer, the term of this patent is extended or adjusted under 35 U.S.C. 154(b) by 284 days.

(21) Appl. No.: 16/382,565

(22) Filed: Apr. 12, 2019

(65) Prior Publication Data
US 2020/0301421 A1    Sep. 24, 2020

(30) Foreign Application Priority Data
Mar. 20, 2019    (KR) ......................... 10-2019-0031943

(51) Int. Cl.
*G05D 1/00* (2006.01)
*G05D 1/02* (2020.01)
*A61B 5/00* (2006.01)

(52) U.S. Cl.
CPC ......... *G05D 1/0088* (2013.01); *A61B 5/4875* (2013.01); *A61B 5/746* (2013.01); *G05D 1/0278* (2013.01); *G05D 2201/0204* (2013.01)

(58) Field of Classification Search
CPC .............. G05D 1/0088; G05D 1/0278; G05D 2201/0204; A61B 5/746; A61B 5/4875
See application file for complete search history.

(56) References Cited

U.S. PATENT DOCUMENTS

| 7,480,569 B2 * | 1/2009 | Wehrlen | G05D 1/0291 701/22 |
| 7,944,368 B2 * | 5/2011 | Carter | B60T 7/16 340/686.6 |
| 9,869,999 B2 * | 1/2018 | Doane | G05D 1/0255 |
| 2004/0260467 A1 * | 12/2004 | Wehrlen | G05D 1/0297 701/36 |

FOREIGN PATENT DOCUMENTS

| KR | 10-2003-0000733 A | 1/2003 |
| KR | 10-1468870 B1 | 12/2014 |

* cited by examiner

*Primary Examiner* — Ramsey Refai
(74) *Attorney, Agent, or Firm* — Hauptman Ham, LLP (57) ABSTRACT

The present invention relates to a golf cart system including a cart body; a control module having a GPS sensor, a receiver for receiving position information of a terminal, golf course information on a cart driving area and a cart driving limit area of the golf club from a server, and information on whether the cart body can enter the golf course with grass, and a driving mode selector for selecting any mode of a cart road driving mode and a cart road and golf course entry driving mode, a server for transmitting the golf course information to the receiver; and the terminal having a GPS sensor for providing the position information thereof to the receiver in real time.

7 Claims, 4 Drawing Sheets

GOLF CART SYSTEM CAPABLE OF CHANGING TRAVELING MODE ACCORDING TO WHETHER ENTERING GOLF COURSE IS POSSIBLE AND GOLF CART CONTROL METHOD USING THE SAME

CROSS REFERENCE TO RELATED APPLICATION

The present application claims the benefit of Korean Patent plication No. 10-2019-0031943 filed in the Korean Intellectual Property Office on Mar. 20, 2019, the entire contents of which are incorporated herein by reference.

BACKGROUND OF THE INVENTION

Field of the Invention

The present invention relates to a golf cart system capable of chancing driving modes according to whether entering a golf course is possible and a golf cart control method using the same, and more particularly, to a golf cart system capable of changing driving modes according to whether entering a golf course is possible and a golf cart control method using the same that are capable of receiving information on a driving area and a driving limit area of the golf course and information on whether a cart body enters the golf course with grass from a server built in a golf club to allow the cart body to be driven only along a cart road or appropriately along both of the cart road and the golf course, thereby permitting the cart body to be driven in the driving mode appropriate for the golf club.

Background of the Related Art

Generally, a golf cart is a vehicle used in a golf club to carry golfers and their golf bag or equipment along a golf course. The golf cart is designed to carry the golfers and their golf equipment conveniently and rapidly around a golf course, which is necessary transportation means in a wide golf club.

A driving mode of the golf cart is divided into a manual driving mode and an automatic driving mode. In case of the manual driving mode, the golf cart is driven through manipulations of a handle, as accelerator, and a brake of a driver of the golf cart, and in case of the automatic driving mode, the golf cart is driven through various control devices mounted thereon, irrespective of the driver's manipulations.

Further, various golf cart systems have been recently developed and proposed to permit their golf cart to recognize and track a terminal carried by a user.

One of conventional technologies is disclosed in Korean Patent Registration No. 10-1468870 in which a radio controlled cart control system for a golf course using an RF transmission speed-based position measurement system is provided with a remote controller, a cart, at least three fixed nodes, and a position calculation node which have respective distance measurement modules adapted to measure distances on the basis of transmission speeds of RF signals, wherein the remote controller and the cart transmit the RF signals, the three fixed nodes receive the RF signals from the remote controller and the cart to transmit arrival time of the received RF signals to the position calculation node, and the position calculation node transmits remote controller and cart position information calculated on the basis of the arrival time of the RF signals to the remote controller and the cart, so that the cart calculates a distance and a direction from the remote controller on the basis of the position information and tracks the remote controller, while maintaining a distance in advance set from the remote controller. In detail, the cart includes a golf bag loading portion, a transportation portion having a golfer boarding portion, a driving part having a front wheel driving motor, a left rear wheel driving motor, and a right rear wheel driving motor to carry the transportation portion, a sensing part having at least four proximity sensors for sensing obstacles in every direction and an inclination sensor adapted to measure an inclination angle, the distance measurement modules adapted to measure the distances on the basis of the transmission speeds of the RF signals, a controller for controlling the driving part on the basis of the position information of the remote controller received from the distance measurement module and the sensed signal of the sensing part, a radio communication part for exchanging information on positions and driving paths with other carts, and a camera module adapted to track the remote controller through the position information of the remote controller to photograph an area around the remote controller so that a golfer's swing motion is displayed, and the controller of the cart controls the cart on the basis of the information on the positions and driving paths of other carts to avoid collision between the carts, provides distances between holes and the remote controller on the basis of the position values in advance stored of the holes of the golf course and the value of the position information of the remote controller, recommends kinds of golf clubs on the basis of the distance between each hole and the remote controller, and if a position control is received from the remote controller, first controls the driving part according to the position control signal, while ignoring the position information and the sensed signal.

Another conventional technology is disclosed in Korean Patent Application Laid-open No. 10-2003-0000733 in which an automatic position control electric cart system a golf course includes an electric cart for loading golf equipment, a main device for determining a current position of the electric cart through a GPS receiver mounted on the electric cart to provide distance information required to play golf and for controlling whether the electric cart is driven in an area in which the electric cart is currently positioned, and a portable remote controller worn on a user and adapted to wirelessly communicate with the main device to allow the electric cart to be maintained at a given distance from the user, while automatically tracking the user, if the electric cart is set to an automatic mode.

According to the above-mentioned conventional technologies, the golf cart recognizes the user or the terminal carried by the user and thus tracks it in real time, but it is actually hard to use the golf cart around a golf course having a given area on which the golf cart cannot be driven so as to protect grass on the given area for a given period of time.

SUMMARY OF THE INVENTION

Accordingly, the present invention has been made in view of the above-mentioned problems occurring in the related art, and it is an object of the present invention to provide a golf cart system capable of changing driving modes according to whether entering a golf course is possible and a golf cart control method using the same that are configured to have a cart body driven manually by means of a user's manipulation or driven automatically by means of a control module and to have a receiver disposed in the control module to receive information on a driving area and a driving limit area of the golf course and information on whether the cart body enters the golf course with grass from a server, so that the cart body is driven automatically to track a terminal in a cart road driving mode in which the cart body is driven along only the cart road and in a cart road and golf course entry driving mode in which the cart body is driven appropriately along both of the cart road and the golf course according to whether the cart body enters the golf course with grass on the basis of the information received by the receiver, thereby controlling the driving of the cart body according to whether the cart body enters the golf course or not to protect holes of the golf course in the golf club.

To accomplish the above-mentioned object, according to one aspect of the present invention, there is provided a golf cart system capable of changing driving modes according to whether entering a golf course is possible, the golf cart system including: a cart body configured to be driven on a cart road and a golf course with grass in a golf club in such a manner as to be driven manually by means of a user's manipulation or driven automatically by means of a control module; the control module having a GPS sensor for providing position information of the cart body, a receiver for receiving position information of a terminal from the terminal, golf course information on a cart driving area and a cart driving limit area of the golf club from a server, and information on whether the cart body can enter the golf course with grass, and a driving mode selector for selecting any one of a cart road driving mode in which if the cart body cannot enter the golf course with grass on the basis of the received information of the receiver, the cart body is automatically driven along the cart road, while tracking the terminal on the basis of the position information of the terminal, and a cart road and golf course entry driving mode in which if the cart body can enter the golf course with grass, the cart body is automatically driven appropriately along the cart road and the golf course with grass, while tracking the terminal on the basis of the position information of the terminal, according to whether the cart body can enter the golf course, to control the driving of the cart body; the server for transmitting the golf course information on the cart driving area and the cart driving limit area of the golf club and the information on whether the cart body can enter the golf course with grass to the receiver; and the terminal having a GPS sensor for providing the position information thereof to transfer the position information thereof to the receiver in real time.

According to the present invention, desirably, the control module includes a sensor adapted to sense whether the user gets on the cart body, so that if the user gets on the cart body, the cart body is driven manually by the user's manipulation, and if the user does not get on the cart body, the cart body is driven automatically by the driving mode selector for selecting any one of the cart road driving mode and the cart road and golf course entry driving mode according to whether the cart body can enter the golf course to control the driving of the cart body.

According to the present invention, desirably, the server includes position information on hole cups of holes and tee shot points in the golf club to transmit the position information on the hole cups of the holes and the tee shot points in the golf club to the receiver, and the cart road driving mode is configured to have an algorithm in which while the cart body is being driven on the cart road in a state of tracking the terminal, the cart body is driven up to a point at which a straight line connecting the hole cup of the hole and the tee shot point along which the cart body is driven and a straight line vertical with respect to the straight line in such a manner as to pass through the terminal cross the cart road.

According to the present invention, desirably, the algorithm defines coordinates as the position information of the tee shot point as x1, y1, coordinates as the position information of the hole cup point as x2, y2, coordinates as the position information of the terminal as x3, y3, and coordinates as the point at which the straight line connecting the hole cup and the tee shot point and the straight line vertical with respect to the straight line in such a manner as to pass through the terminal cross the cart road as x, y, and the coordinates x1, x2, y2, x3 and y3 are substituted for a mathematical formula, $$y = \frac{(y_1 + y_2)}{(x_2 - x_1)} * x + x_3 + \frac{(y_2 + y_1)}{(x_2 - x_1)} * y_3,$$

so that the cart body as driven up to the point at which the straight line connecting the hole cup and the tee shot point and the straight line vertical with respect to the straight line in such a manner as to pass through the terminal cross the cart road.

According to the present invention, desirably, the server includes virtual path information having a plurality of coordinates within a set range spaced apart from the circumstance of the driving limit area of each hole by a given distance in an outward direction to transmit the virtual path information to the receiver, and at the time when the cart body enters the set range of the driving limit area, the cart road and golf course entry driving mode includes a virtual path tracking mode in which the cart body is driven along the virtual path, while tracking the terminal.

According to the present invention, desirably, the terminal includes a measurer having a measuring member for measuring the body composition of the user and an analysis module for analyzing the body composition data measured by the measuring member to calculate total body water, comparing the calculated total body water with total body water in advance set, and transmitting a signal to an alarm if the calculated total body water is less than the total body water in advance set by 3%, and the control module includes the alarm adapted to generate a warning sound if the signal from the analysis module is received.

To accomplish the above-mentioned object, according to another aspect of the present invention, there is provided a golf cart control method using a golf cart system including: the golf course information receiving step of allowing a receiver to receive information on a driving area and a driving limit area in a golf course and information on whether a cart body can enter the golf course with grass from a server; the driving mode selecting step of allowing a driving mode to be selected as any one of a cart road driving mode and a cart road and golf course entry driving mode according to whether the cart body can enter the golf course on the basis of the information received by the receiver; and the cart body control step of allowing the cart body to be controlled by the set driving mode in the driving mode selecting step.

BRIEF DESCRIPTION OF THE DRAWINGS

The above and other objects, features and advantages of the present invention will be apparent from the following detailed description of one of the embodiments of the invention in conjunction with the accompanying drawings, in which.

DETAILED DESCRIPTION OF THE INVENTION

The present invention relates to a golf cart system capable of changing driving modes according to whether entering a golf course is possible and a golf cart control method using the same that receive golf course information on an area in which a cart body is driven and a limit area in which driving of the cart body is limited and information on whether the cart body enters the golf course with grass from a server built in a golf club to allow the cart body to be driven along only a cart road or appropriately along both of the cart road and the golf course according to whether the cart body enters the golf course, so that the cart body can be driven in the driving mode adequate for the golf club.

Hereinafter, an explanation on a configuration and an operation of a golf cart system according to the present invention is given with reference to FIGS. 1 to 5.

Figure 1:
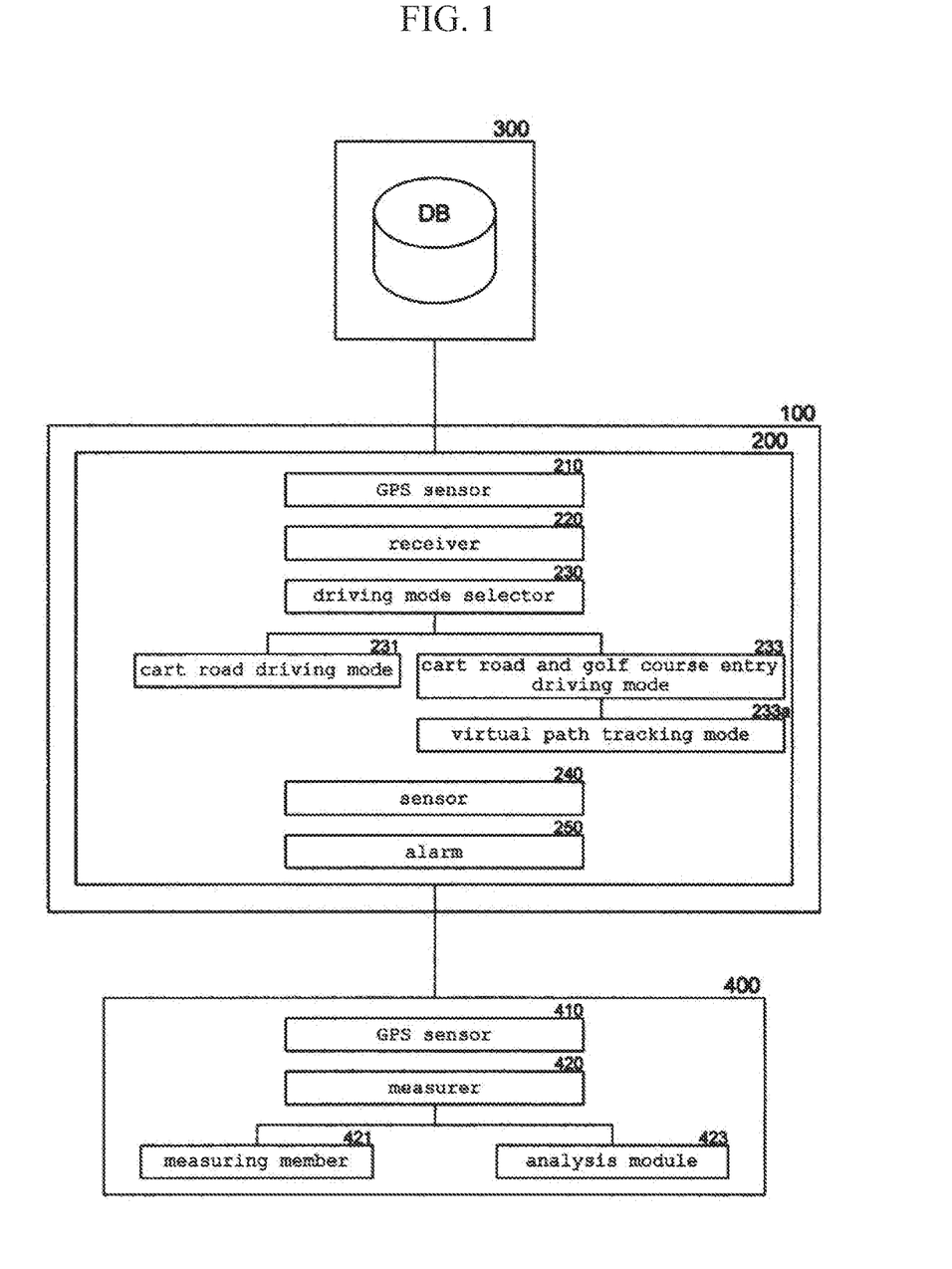
FIG. 1 is a block diagram showing a golf cart system capable of changing driving modes according to whether entering a golf course is possible according to the present invention.
Figure 2:
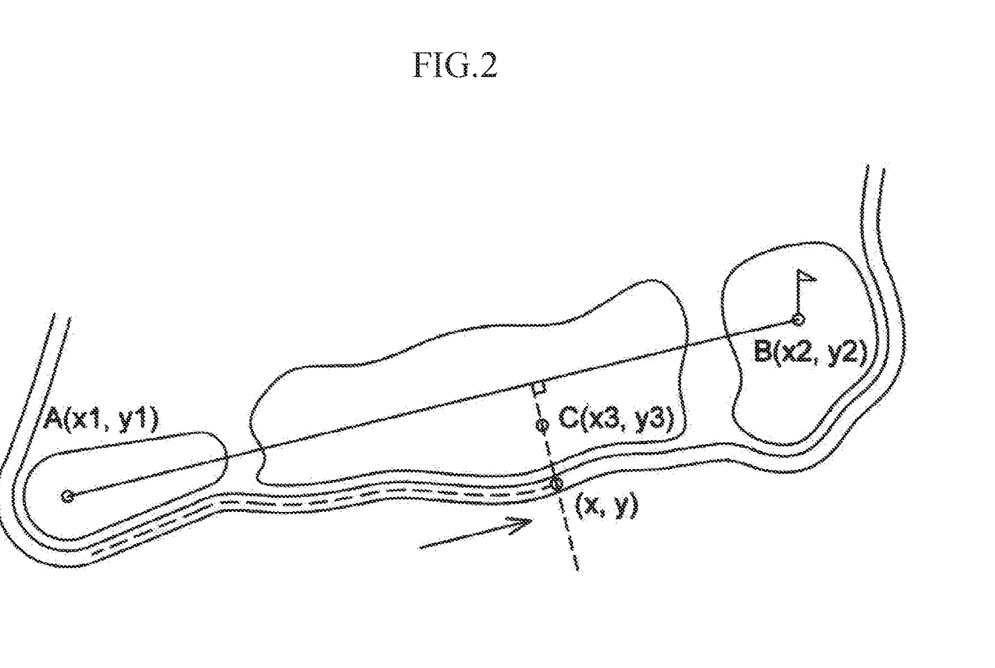
FIG. 2 is a top view showing a cart road driving mode in the golf cart system according to the present invention.

First of all, the configuration of the golf cart system capable of changing driving modes according to whether entering a golf course is possible according to the present invention is explained with reference to FIGS. 1 to 3. As shown, the golf cart system according to the present invention includes: a cart body 100 configured to be driven on a cart road and a golf course with grass in a golf club in such a manner as to be driven manually by means of a user's manipulation or driven automatically by means of a control module 200; the control module 200 having a GPS sensor 210 for providing position information of the cart body 100, a receiver 220 for receiving position information of a terminal 400 from the terminal 400, golf course information on a cart driving area and a cart driving limit area of the golf club from a server 300, and information on whether the cart body 100 can enter the golf course with grass, and a driving mode selector 230 for selecting any one of a cart road driving mode 231 is which if the cart body 100 cannot enter the golf course with grass on the basis of the received information of the receiver 220, the cart body 100 is automatically driven along the cart road, while tracking the terminal 400 on the basis of the position information of the terminal 400, and a cart road and golf course entry driving mode 233 in which if the cart body 100 can enter the golf course with grass, the cart, body 100 is automatically driven appropriately along the cart road and the golf course with grass, while tracking the terminal 400 on the basis of the position information of the terminal 400, according to whether the cart body 100 can enter the golf course, to control the driving of the cart body 100; the server 300 for transmitting the golf course information on the cart driving area and the cart driving limit area of the golf club and the information on whether the cart body 100 can enter the golf course with grass to the receiver 220; and the terminal 400 having a GPS sensor 410 for providing the position information thereof to transfer the position information thereof to the receiver 220 in real time.

The cart body 100 on which a user gets with his or her golf bag or the like is configured to be driven on the cart road and the golf course with grass in the golf club in such a manner as to be driven manually by means of a user's manipulation or driven automatically by means of the control module 200 as will be in detail discussed later.

The control module 200 includes the GPS sensor 210, the receiver 220 and the driving mode selector 230, and desirably, the control module 200 is disposed on one side of the cart body 100.

The GPS sensor 210 serves to provide the position information of the cart body 100 and is interlocked with the receiver 220 to provide the position of the cart body 100 to the receiver 220. If necessary, the GPS sensor 210 may provide the position of the cart body 100 to the server 300 of a golf club control center connected thereto through separate communication means.

The receiver 220 serves to receive and store the position information of the terminal 400 from the terminal 400, the golf course information on the cart driving area and the cart driving limit area of the golf club from the server 300, and the information on whether the cart body 100 can enter the golf course with grass to provide the received information to the driving mode selector 230, so that the driving mode selector 230 can select any one of the cart road driving mode 231 and the cart road and golf course entry driving mode 233, while tracking the terminal 400 carried by the user on the basis of the received information.

The driving mode selector 230 serves to select any one of the cart road driving mode 231 in which if the cart body 100 cannot enter the golf course with grass on the basis of the received information of the receiver 220, the cart body 100 is driven automatically along the cart road, while tracking the terminal 400 on the basis of the position information of the terminal 400, and the cart road and golf course entry driving mode 233 in which if the cart body 100 can enter the golf course with grass, the cart body 100 is driven automatically along both of the cart road and the golf course with grass, while tracking the terminal 400 on the basis of the position information of the terminal 400, according to whether the cart body 100 can enter the golf course, to control the driving of the cart body 100.

In detail, the driving mode selector 230 controls the driving modes and driving of the cart body 100 according to whether the cart body 100 enters the golf course or not so as to protect the grass of the golf course, so that the cart body 100 is driven along only the cart road or driven appropriately along both of the cart road and the golf course, thereby protecting the grass of the golf course and making it impossible to enter the golf course for a given period of time during which repair work is planned.

The server 300 serves to transmit the golf course information on the cart driving area and the cart driving limit area in the golf club and the information on whether the cart body 100 can enter the golf course with grass to the receiver 220.

If the golf course information is suddenly changed, during the cart body 100 is used by the user with the terminal 400, the server 300 transmits the changed information to the receiver 220 of the control module 200 in real time so as to allow the cart body 100 to immediately handle the suddenly changed situation.

Further, the server 300 is a general server located in the control center where a control system of the golf club is disposed, and otherwise, it is a web site operated in the golf club.

The terminal 400 has the GPS sensor 410 adapted to provide the position information thereof to transfer the position information thereof to the receiver 220 in real time.

In this case, the terminal 400 is the same mechanical device as a general smartphone, to which various communication systems are applied, and desirably, the terminal 400 whose interior is basically configured to be interlocked with the control module 200 for controlling the cart body 100.

The control module 200 further includes a sensor 240 adapted to sense whether the user gets on the cart body 100, so that if the user gets on the cart body 100, the cart body 100 is driven manually by the user's manipulation, and if the user does not get on the cart body 100, the cart body 100 is driven automatically by the driving mode selector 230 adapted to select any one of the cart road driving mode 231 and the cart road and golf course entry driving mode 233 according to whether the cart body 100 can enter the golf course to control the driving of the cart body 100.

In detail, at the time when the sensor 240 senses that the user with the terminal 400 gets on the cart body 100, the cart road driving mode 231 or the cart road and golf course entry driving mode 233 of the driving mode selector 230 is turned off, thereby allowing the cart body 100 to be driven manually by the user's manipulation, and contrarily, at the time when the sensor 240 senses that the user with the terminal 400 gets off the cart body 100 or walks, without getting on the cart body 100, the cart road driving mode 231 or the cart road and golf course entry driving mode 233 of the driving mode selector 230 is turned on, thereby allowing the cart body 100 to be driven to track the terminal 400.

The server 300 includes position information on hole cups of holes and tee shot points in the golf course to transmit the position information on the hole cups of the holes and the tee shot points in the golf course to the receiver 220, and the cart road driving mode 231 is configured to have an algorithm a1 in which while the cart body 100 is being driven on the cart road in a state of tracking the terminal 400, it is driven up to a point at which a straight line connecting the hole cup of the hole and the tee shot point along which the cart body 100 is driven and a straight line vertical with respect to the straight line in such a manner as to pass through the terminal 400 cross the cart road.

In this case, the algorithm a1 defines coordinates as the position information of the tee shot point as x1, y1, coordinates as the position information of the hole cup point as x2, y2, coordinates as the position information of the terminal 400 as x3, y3, and coordinates as the point at which the straight line connecting the hole cup and the tee shot point and the straight line vertical with respect to the straight line in such a manner as to pass through the terminal 400 cross the cart road as x, v, and next, the coordinates x1, y1, x2, y2, x3 and y3 are substituted for a mathematical formula, $$y = \frac{(y_1 + y_2)}{(x_2 - x_1)} * x + x_3 + \frac{(y_2 + y_1)}{(x_2 - x_1)} * y_3,$$

so that the cart body 100 is driven up to the point at which the straight line connecting the hole cup and the tee shot point and the straight line vertical with respect to the straight line in such a manner as to pass through the terminal 400 cross the cart road.

First, the xi is the latitude of the tee shot point, vi is the longitude of the tee shot point, x2 is the latitude of the hole cup point, y2 is the longitude of the hole cup point, x3 is the latitude of the terminal carried by the user, y3 is the longitude of the terminal carried by the user, x is the latitude of the cart body 100, and y is the longitude of the cart body 100.

Now, an explanation on the above mathematical formula, $$y = \frac{(y_1 + y_2)}{(x_2 - x_1)} * x + x_3 + \frac{(y_2 + y_1)}{(x_2 - x_1)} * y_3$$

will be given with reference to FIG. 2.

So as to obtain the above mathematical formula, first, a linear function passing through two points is indicated by y=ax+b, A(x1, y1) indicates the coordinates of the tee shot point, and B(x2, y2) indicates the coordinates of the hole cup point.

At this time, $$\text{Inclination } a = \frac{(x_2 - x_1)}{(y_2 + y_1)} \quad (1)$$

$$\text{Intercept } b = x_1 - ay_1 \quad (2)$$
$$= x_1 - \frac{(x_2 - x_1)}{(y_2 + y_1)} * y_1$$

At the time when the inclination and the coordinates (position of the terminal, x3 and y3) of one point are recognized, the linear function is indicated by y=cx+d.

$$\text{Inclination } c = -\frac{1}{a} \quad (3)$$

$$\text{Intercept } d = x_3 - c * y_3 \quad (4)$$
$$= x_3 - \left(-\frac{1}{a}\right) * y_3$$
$$= x_3 + \left(\frac{1}{\frac{(x_2 - x_1)}{(y_2 - y_1)}}\right) * y_3$$
$$= x_3 + \frac{(y_2 - y_1)}{(x_2 - x_1)} * y_3$$

The values of the mathematical formulas (1), (2), (3) and (4) are substituted for the following formulas to obtain a mathematical formula (5).

$$y = cx + d \quad (5)$$
$$= \left(\frac{-1}{a}\right) * x + d$$
$$= \left(\frac{-1}{\frac{(x_2 - x_1)}{(y_2 - y_1)}}\right) * x + \left(x_3 + \frac{(y_2 - y_1)}{(x_2 - x_1)} * y_3\right)$$

The mathematical formula (5) is simplified to obtain the following mathematical formula (6) through which the cart body 100 is driven up to the point x, y at which the straight line connecting the tee shot point x1, y1 and the hole cup point x2, y2 and the straight line vertical with respect to the straight line in such a manner as to pass through the terminal 400 cross the cart road.

$$y = \frac{(y_2 - y_1)}{(x_2 - x_1)} * x + x_3 + \frac{(y_2 - y_1)}{(x_2 - x_1)} * y_3 \qquad (6)$$

The server 300 includes virtual path information having a plurality of coordinates within a set range spaced apart from the circumstance of the driving limit area of each hole by a given distance in an outward direction so as to transmit the virtual path information to the receiver 220, and at the time when the cart body 100 enters the set range of the driving limit area, the cart road and golf course entry driving mode 233 includes a virtual path tracking mode 233a in which the cart body 100 is driven along the virtual path, while tracking the terminal 400.

Figure 3:
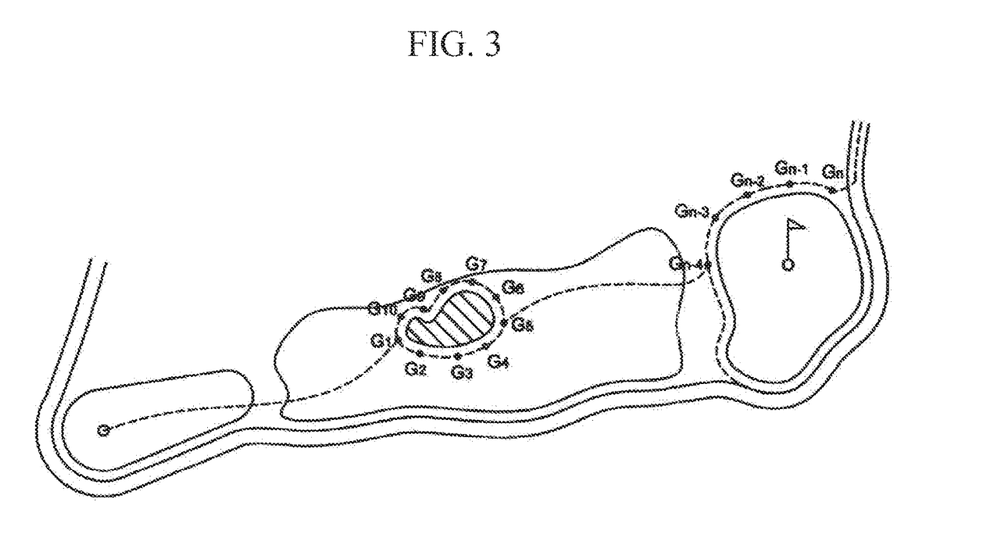
FIG. 3 is a top view showing a cart road and golf course entry driving mode is the golf cart system according to the present invention.

In detail, as shown in FIG. 3, the server 300 has the virtual path information having the plurality of coordinates within the set range spaced apart from the circumstance of the driving limit area, such as a bunker of the golf course, a dangerous place like a hazard, and putting green of the golf course, where entering the cart body 100 is impossible, by the given distance in the outward direction.

In more detail, if the user with the terminal 400 enters the hazard or the putting green of the golf course, the cart body 100, which is driven to track the terminal 400, approaches the hazard or the putting green of the golf course as the driving limit area and finally enters the set range in which the virtual path having the plurality of coordinates is formed, so that the cart body 100 is driven along virtual path coordinates G1, G2, G3, G4, G5, . . . , Gn–1, and Gn closest to the user with the terminal 400, thereby tracking the user with the terminal 400.

If the user with the terminal 400 escapes from the driving limit area such as the hazard or the putting green of the golf course, the virtual path tracking mode 233a changes into the cart road and golf course entry driving mode 233, thereby desirably allowing the cart body 100 to be driven to track the terminal 400.

The terminal 400 includes a measurer 420 having a measuring member 421 for measuring the body composition of the user and an analysis module 423 for analyzing the body composition data measured by the measuring member 421 to calculate total body water, comparing the calculated total body water with total body water in advance set, and transmitting a signal to an alarm 250 if the calculated total body water is less than the total body water in advance set by 3%, and the control module 200 includes the alarm 250 adapted to generate a warning sound at the time when it receives the signal from the analysis module 423.

In this case, the measuring member 421 of the measurer 420 is disposed on one side of the outer surface of the terminal 400 and includes a general electrode coming contact with the user's skin so as to measure the body composition of the user, and the analysis module 423 analyzes the body composition data measured by the measuring member 421 to calculate total body water in the user's body. The analysis module 423 sets the total body water calculated on the basis of the body composition measured before the user starts to play golf, and if the total body water is less than the set total body water by 3% while the user is playing golf, the analysis module 423 transmits the analyzed signal to the alarm 250.

In detail, if the user keeps playing golf even in a state where he or she does not recognize lack of his or her total body water through high concentration, the measurer 420 causes the alarm 250 to generate the warning sound so that he or she approaches the cart body 100 to drink water or beverage prepared in the cart body 100.

Now, an explanation on a golf cart control method using the golf cart system having the above-mentioned configuration will be given with reference to FIGS. 4 and 5.

Figure 4:
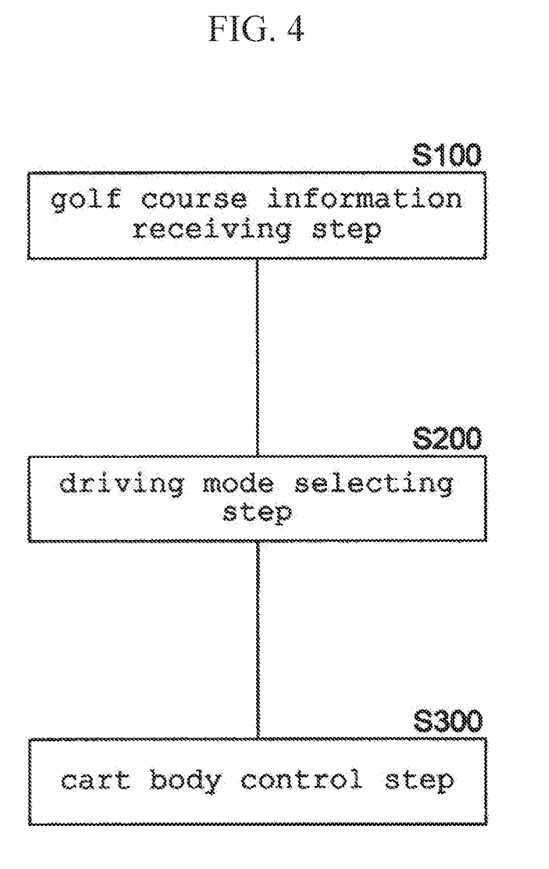
FIG. 4 is a flow chart showing a golf cart control method according to the present invention.
Figure 5:
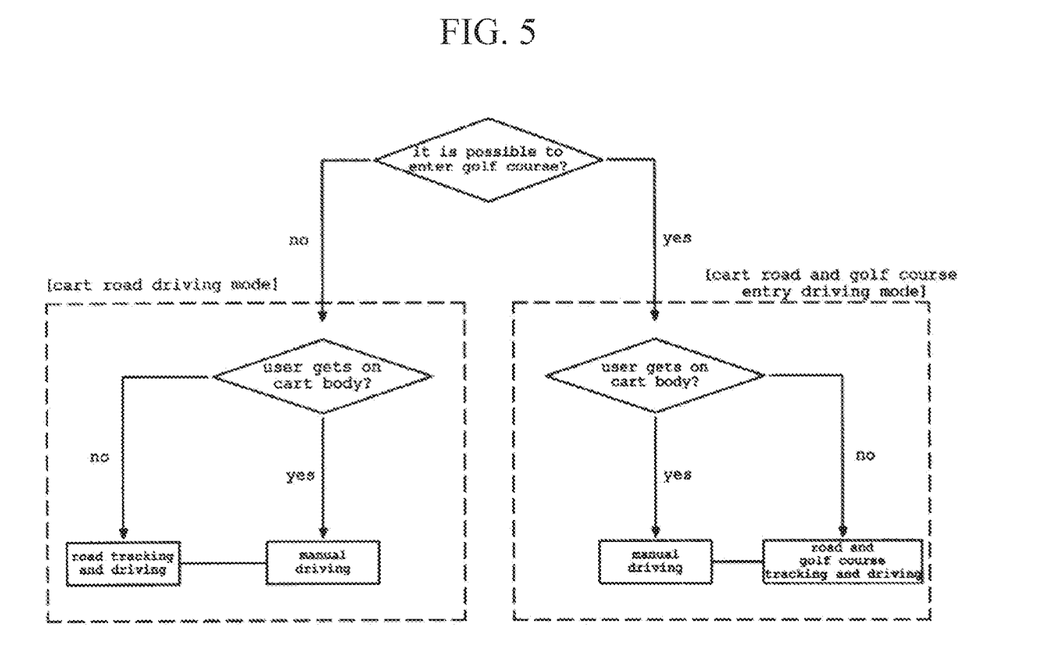
FIG. 5 is a flow chart showing the driving modes in the golf cart control method according to the present invention according to whether entering the golf course is possible.

As shown in FIGS. 4 and 5, the golf cart control method using the golf cart system according to the present invention includes: the golf course information receiving step S100 of allowing the receiver 220 to receive the information on the driving area and the driving limit area in the golf course and the information on whether the cart body 100 can enter the golf course with grass from the server 300; the driving mode selecting step S200 of allowing the driving mode to be selected as any one of the cart road driving mode 231 and the cart road and golf course entry driving mode 233 according to whether the cart body 100 can enter the golf course on the basis of the information received by the receiver 220; and the cart body control step S300 of allowing the cart body 100 to be controlled by the set driving mode in the driving mode selecting step S200.

The golf course information receiving step S100 is carried out by receiving the information on the driving area and the driving limit area in the golf course where the user plays golf and the information on whether the cart body 100 can enter the golf course with grass, so that the cart body 100 is driven in the driving mode selected in the driving mode selecting step S200.

The driving mode selecting step S200 is carried out by selecting any one of the cart road driving 231 and the cart road and golf course entry driving mode 233 according to whether the cart body 100 can enter the golf course on the basis of the information received by the receiver 220, so that the cart body 100 can be driven along only the cart road or appropriately along both of the cart road and the golf course, thereby being used in an appropriate driving mode to cope with an impossibility in the golf course entry of the cart body 100 for a given period of time for grass protection and repair work.

As described above, the golf cart system capable of changing the driving modes according to whether entering the golf course is possible and the golf cart control method using the same are capable of allowing the cart body to be driven to track the terminal through the control module according to the position information of the terminal and allowing the driving mode of the cart body to be selected by the control module according to whether the cart body enters respective holes in the golf course with grass, so that the cart body can be driven along only the cart road or appropriately along both of the cart road and the golf course, thereby permitting the driving modes of the cart body to be controlled integrally through the server built in the golf club to cope with an impossibility in the golf course entry of the cart body for a given period of time for grass protection and repair work and thus improving the conveniences in management.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A golf cart system capable of changing driving modes according to whether entering a golf course is possible, the golf cart system comprising:
 a cart body (100) configured to be driven on a cart road and a golf course with grass is a golf club in such a manner as to be driven manually by means of a user's manipulation or driven automatically by means of a control module (200);

the control module (200) having a GPS sensor (210) for providing position information of the cart body (100), a receiver (220) for receiving position information of a terminal (400) from the terminal (400), golf course information on a cart driving area and a cart driving limit area of the golf club from a server (300), and information on whether the cart body (100) can enter the golf course with grass, and a driving mode selector (230) for selecting any one of a cart road driving mode (231) in which if the cart body (100) cannot enter the golf course with grass on the basis of the received information of the receiver (220), the cart body (100) is automatically driven along the cart road, while tracking the terminal (400) on the basis of the position information of the terminal (400), and a cart road and golf course entry driving mode (233) in which if the cart body (100) can enter the course with grass, the cart body (100) is automatically driven appropriately along the cart road and the golf course with grass, while tracking the terminal (400) on the basis of the position information of the terminal (400), according to whether the cart body (100) can enter the golf course, to control the driving of the cart body (100);

the server (300) for transmitting the golf course information on the cart driving area and the cart driving limit area of the golf club and the information on whether the cart body (100) can enter the golf course with grass to the receiver (220); and the terminal (400) having a GPS sensor (410) for providing the position information thereof to transfer the position information thereof to the receiver (220) is real time.

2. The golf cart system according to claim 1, wherein the control module (200) comprises a sensor (240) adapted to sense whether the user gets on the cart body (100), so that if the user gets on the cart body (100), the cart body (100) is driven manually by the user's manipulation, and if the user does not get on the cart body (100), the cart body (100) is driven automatically by the driving mode selector (230) for selecting any one of the cart road driving mode (231) and the cart road and golf course entry driving mode (233) according to whether the cart body (100) can enter the golf course to control the driving of the cart body (100).

3. The golf cart system according to claim 1, wherein. the server (300) comprises position information on hole cups of holes and tee shot points in the golf club to transmit the position information on the hole cups of the holes and the tee shot points is the golf club to the receiver (220), and the cart road driving mode (231) configured to have an algorithm (a1) in which while the cart body (100) is being driven on the cart road in a state of tracking the terminal (400), the cart body (100) is driven up to a point at which a straight line connecting the hole cup of the hole and the tee shot point along which the cart body (100) is driven and a straight line vertical with respect to the straight line in such a manner as to pass through the terminal (400) cross the cart road.

4. The golf cart system according to claim 3, wherein the algorithm (a1) defines coordinates as the position information of the tee shot point as x1, y1, coordinates as the position information of the hole cup point as x2, y2, coordinates as the position information of the terminal (400) as x3, y3, and coordinates as the point at which the straight line connecting the hole cup and the tee shot point and the straight line vertical with respect to the straight line in such a manner as to pass through the terminal (400) cross the cart road as x, y, and the coordinates x1, y1, x2, y2, x3 and y3 are substituted for a mathematical formula, $$y = \frac{(y_2 - y_1)}{(x_2 - x_1)} * x + x_3 + \frac{(y_2 - y_1)}{(x_2 - x_1)} * y_3,$$

so that the cart body (100) is driven up to the point at which the straight line connecting the hole cup and the tee shot point and the straight line vertical with respect to the straight line in such a manner as to pass through the terminal (400) cross the cart road.

5. The golf cart system according to claim 1, wherein the server (300) comprises virtual path information having a plurality of coordinates within a set range spaced apart from the circumstance of the driving limit area of each hole by a given distance in an outward direction to transmit the virtual path information to the receiver (220), and at the time when the cart body (100) enters the set range of the driving limit area, the cart road and golf course entry driving mode (233) comprises a virtual path tracking mode (233a) in which the cart body (100) is driven along the virtual path, while tracking the terminal (400).

6. The golf cart system according to claim 1, wherein the terminal (400) comprises a measurer (420) having a measuring member (421) for measuring the body composition of the user and an analysis module (423) for analyzing the body composition data measured by the measuring member (421) to calculate total body water, comparing the calculated total body water with total body water in advance set, and transmitting a signal to an alarm (250) if the calculated total body water is less than the total body water in advance set by 3%, and the control module (200) comprises the alarm (250) adapted to generate a warning sound if the signal from the analysis module (423) is received.

7. A golf cart control method using the golf cart system according to claim. 1, the method comprising:

the golf course information receiving step (S100) of allowing the receiver (220) to receive the information on the driving area and the driving limit area in the golf course and the information on whether the cart body (100) can enter the golf course with grass from the server (300);

the driving mode selecting step (S200) of allowing the driving mode to be selected as any one of the cart road driving mode (231) and the cart road and golf course entry driving mode (233) according to whether the cart body (100) can enter the golf course on the basis of the information received by the receiver (220); and the cart body control step (S300) of allowing the cart body (100) to be controlled by the set driving mode in the driving mode selecting step (S200).

* * * * *